US012765841B2

(12) United States Patent
Taniguchi et al.

(10) Patent No.: US 12,765,841 B2
(45) **Date of Patent: *Oct. 20, 2026**

(54) MRI IMAGING SYSTEM WITH EXAMINATION TABLE APPARATUS HAVING INDEPENDENTLY SLIDABLE COIL CONNECTORS

(71) Applicant: FUJIFILM Corporation, Tokyo (JP)

(72) Inventors: Takeshi Taniguchi, Tokyo (JP); Kazuyuki Kato, Tokyo (JP); Satoshi Iizuka, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 18/946,835

(22) Filed: Nov. 13, 2024

(65) Prior Publication Data

US 2025/0160756 A1 May 22, 2025

(30) Foreign Application Priority Data

Nov. 16, 2023 (JP) ................................ 2023-195258

(51) Int. Cl.
*A61B 5/00* (2006.01)
*A61B 5/055* (2006.01)
*G01R 33/34* (2006.01)

(52) U.S. Cl.
CPC .............. *A61B 5/704* (2013.01); *A61B 5/055* (2013.01); *G01R 33/34007* (2013.01)

(58) Field of Classification Search
CPC .......................... A61B 5/704; G01R 33/56375
See application file for complete search history.

(56) References Cited

U.S. PATENT DOCUMENTS

2007/0035301 A1* 2/2007 Nakabayashi ......... G01R 33/28 324/318
2021/0030306 A1* 2/2021 Leussler ................ A61B 5/055
2021/0199738 A1 7/2021 Ikeda et al.
2023/0301597 A1* 9/2023 Spring ................... A61B 5/055

FOREIGN PATENT DOCUMENTS

JP H06315473 11/1994

OTHER PUBLICATIONS

THK, <https://www.thk.com/eu/en/news/products/article-04082022-1.html>, (Aug. 4, 2022), retrieved on Jun. 23, 2026. (Year: 2022).*
"Office Action of Related, U.S. Appl. No. 18/946,838", issued on Apr. 6, 2026, p. 1-p. 24.

* cited by examiner

*Primary Examiner* — Keith M Raymond
*Assistant Examiner* — Ashish S. Jasani
(74) *Attorney, Agent, or Firm* — JCIPRNET

(57) ABSTRACT

An aspect of the present invention relates to an examination table apparatus used in a medical imaging apparatus, the examination table apparatus including: a top plate on which a subject is placed; and a plurality of connectors that are provided on the top plate and that connect a coil for capturing an image of the subject, in which the plurality of connectors are provided on both sides of the top plate in a lateral direction, with one or more connectors on each side, and are slidable with respect to the top plate in a part of the top plate in a longitudinal direction. The examination table apparatus may handle the connection of a wide variety of coils while shortening a cable length.

14 Claims, 17 Drawing Sheets

MRI IMAGING SYSTEM WITH EXAMINATION TABLE APPARATUS HAVING INDEPENDENTLY SLIDABLE COIL CONNECTORS

CROSS-REFERENCE TO RELATED APPLICATION

The present application claims priority under 35 U.S.C § 119(a) to Japanese Patent Application No. 2023-195258 filed on Nov. 16, 2023, which is hereby expressly incorporated by reference, in its entirety, into the present application.

BACKGROUND OF THE INVENTION

1. Field of the Invention

The present invention relates to an examination table apparatus and a medical imaging system, and more particularly to an examination table apparatus including a slidable connector and a medical imaging system comprising such an examination table apparatus.

2. Description of the Related Art

In a medical imaging apparatus, such as a magnetic resonance imaging apparatus (MRI apparatus), it is known that a connector for connecting a coil used for imaging is provided in an examination table apparatus. It is preferable that a cable for connecting the coil and the connector is short, and thus a connector that can be handled by a short cable by sliding on a top plate of the examination table apparatus is used (for example, see JP1994-315473A (JP-H06-315473A)).

SUMMARY OF THE INVENTION

In the technique described in JP1994-315473A (JP-H06-315473A), one slidable connector is provided on one side of the examination table, but it may be necessary to provide connectors on both sides of the top plate depending on a type or a size of the coil used for the imaging. In addition, a plurality of types or a plurality of coils may be attached depending on the number of imaging parts or the like. In this case, in a case in which the connector is provided only on one side of the examination table, the cable length cannot be sufficiently shortened. In addition, in a case in which the connector is slid over the entire length of the examination table as in JP1994-315473A (JP-H06-315473A), the cable may be lengthened, and thus a problem of heat generation or electrical coupling may occur.

As described above, in the related art, it is not possible to handle the connection of a wide variety of coils while shortening the cable length.

The present invention has been made in view of such circumstances, and an object of the present invention is to provide an examination table apparatus that can handle the connection of a wide variety of coils while shortening a cable length, and a medical imaging system comprising such an examination table apparatus.

In order to achieve the above-described object, a first aspect of the present invention relates to an examination table apparatus used in a medical imaging apparatus, the examination table apparatus comprising: a top plate on which a subject is placed; and a plurality of connectors that are provided on the top plate and that connect a coil for capturing an image of the subject, in which the plurality of connectors are provided on both sides of the top plate in a lateral direction, with one or more connectors on each side, and are slidable with respect to the top plate in a part of the top plate in a longitudinal direction.

According to the first aspect, the plurality of connectors are provided with one or more on each of both sides of the top plate in the lateral direction, and are slidable with respect to the top plate in a part of the top plate in the longitudinal direction, so that it is possible to handle the connection of a wide variety of coils while shortening a cable length.

In the first aspect and each of the following aspects, a plurality of connectors may be provided in at least one side of the top plate in the lateral direction. The sliding of the connector may be performed manually or automatically.

A second aspect relates to the examination table apparatus according to the first aspect, in which a plurality of openings or a plurality of grooves are formed on both sides of the top plate in the lateral direction, in a part of the top plate in the longitudinal direction, and the plurality of connectors are slidable in the plurality of openings or the plurality of grooves. The second aspect specifies one aspect of a mechanism for sliding the connector.

A third aspect relates to the examination table apparatus according to the second aspect, further comprising: a plurality of support members that support the plurality of connectors; and a plurality of holding members that hold the plurality of support members, that are disposed on both sides of the top plate in the lateral direction and projected in the longitudinal direction, and that are fixed to the top plate, in which the plurality of support members are slid with respect to the plurality of holding members to slide the plurality of connectors with respect to the top plate. Although it is difficult to dispose the connector on both sides of the examination table in the mechanism for sliding the connector by using an arm connected by a hinge as in JP1994-315473A (JP-H06-315473A) (JP1994-315473A (JP-H06-315473A), FIG. 1B), according to the third aspect, it is easy to dispose the connector on both sides of the examination table (top plate).

A fourth aspect relates to the examination table apparatus according to the third aspect, in which the holding member holds a horizontal-direction end part of the support member. The fourth aspect defines one aspect of a specific configuration of the holding member.

A fifth aspect relates to the examination table apparatus according to the third or fourth aspect, in which the holding member holds at least a part of a vertical-direction lower surface of the support member. The fifth aspect defines another aspect of the specific configuration of the holding member.

A sixth aspect relates to the examination table apparatus according to any one of the third to fifth aspects, in which a gap between the plurality of connectors and the plurality of openings or the plurality of grooves is shielded by at least one of the support member or the holding member. According to the sixth aspect, it is possible to prevent an article used in the examination table apparatus or the periphery thereof from falling off from the gap between the connector and the opening or the groove, the article or a finger of the subject from being pinched in the gap, or the liquid from being spilled, and the safety of the examination table apparatus is improved.

A seventh aspect relates to the examination table apparatus according to any one of the first to sixth aspects, further comprising: a processor; and a sliding mechanism that moves the plurality of connectors in the longitudinal direction, in which the processor is configured to: acquire information on the subject; and slide the plurality of connectors by controlling the sliding mechanism based on the acquired information. The seventh aspect defines an aspect in which the sliding of the connector is automatically controlled, and according to such an aspect, the user's time and effort can be saved.

An eighth aspect relates to the examination table apparatus according to the seventh aspect, in which the processor is configured to: acquire an imaging condition of a medical image for the subject as the information on the subject.

A ninth aspect relates to the examination table apparatus according to the seventh or eighth aspect, in which the processor is configured to: determine a sliding target connector among the plurality of connectors and a sliding position of the sliding target connector, based on the information on the subject, and slide the sliding target connector to the sliding position.

A tenth aspect provides the examination table apparatus according to any one of the first to ninth aspects, in which, in a case in which the subject in a state in which the coil is attached is placed on the top plate, the plurality of connectors are movable to a position overlapping a range in which the coil is present in the longitudinal direction of the top plate. According to the tenth aspect, it is possible to shorten the cable routing.

An eleventh aspect relates to the examination table apparatus according to any one of the first to tenth aspects, in which the plurality of connectors are slidable independently of each other.

A twelfth aspect relates to the examination table apparatus according to any one of the first to tenth aspects, in which one connector among the plurality of connectors and the other connector among the plurality of connectors are slidable in conjunction with each other.

A thirteenth aspect relates to the examination table apparatus according to any one of the first to twelfth aspects, in which the medical imaging apparatus is a magnetic resonance imaging apparatus.

In order to achieve the above-described object, a fourteenth aspect of the present invention relates to a medical imaging system comprising: the examination table apparatus according to any one of the first to thirteenth aspects; and the medical imaging apparatus. According to the fourteenth aspect, as in the first aspect, it is possible to handle the connection of a wide variety of coils while shortening the cable length.

A fifteenth aspect relates to the medical imaging system according to the fourteenth aspect, in which coils for imaging different parts of the subject are connected to one connector and the other connector among the plurality of connectors.

A sixteenth aspect relates to the medical imaging system according to the fourteenth or fifteenth aspect, in which a coil for imaging a specific part of the subject is connectable to one connector provided on one side of the top plate in the lateral direction of the top plate among the plurality of connectors, and the other connector provided on the other side of the top plate in the lateral direction of the top plate among the plurality of connectors. According to the sixteenth aspect, the coil for imaging the specific part of the subject can be connected to the connectors on both sides, and this aspect is effective in a case in which a large-sized coil or a coil provided with a plurality of cables is used. It should be noted that examples of the "coil for imaging a specific part" include a coil for a spine, but the present invention is not limited thereto.

As described above, with the examination table apparatus and the medical imaging system according to the aspects of the present invention, it is possible to handle the connection of a wide variety of coils while shortening the cable length.

BRIEF DESCRIPTION OF THE DRAWINGS

FIGS. 10A to 10F are diagrams showing a variation of the sliding mechanism.

DESCRIPTION OF THE PREFERRED EMBODIMENTS

Hereinafter, preferred embodiments of a medical imaging system and an examination table apparatus according to an embodiment the present invention will be described with reference to the accompanying drawings. It should be noted that, in the accompanying drawings, in some cases, some components are not shown for convenience of description. Further, the accompanying drawings do not show accurate shapes and dimensions of the examination table apparatus and the medical imaging system.

First Embodiment

Entire Configuration of Magnetic Resonance Imaging System

Figure 1:
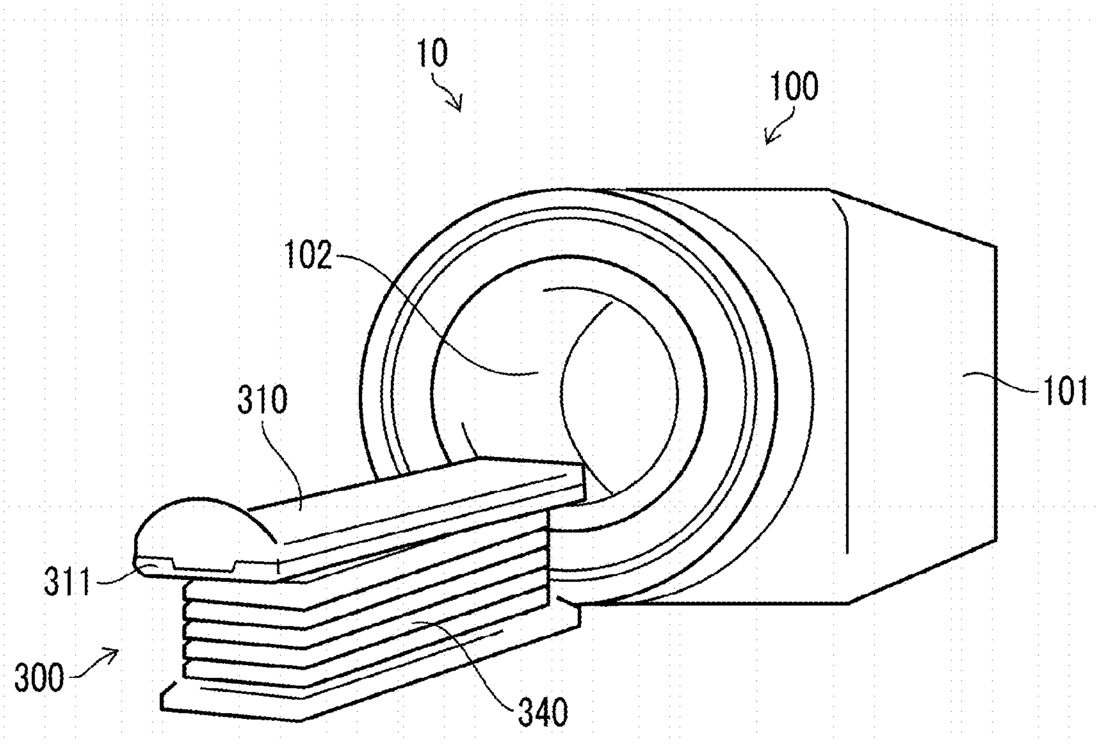
FIG. 1 is a diagram showing an entire configuration of a magnetic resonance imaging system according to a first embodiment.

First, an entire configuration of the magnetic resonance imaging system will be described. As shown in FIG. 1, a magnetic resonance imaging system 10 (medical imaging system) according to the first embodiment of the present invention comprises a magnetic resonance imaging apparatus 100 (medical imaging apparatus) and an examination table apparatus 300 (examination table apparatus).

The magnetic resonance imaging apparatus 100 is an apparatus that acquires a tomographic image of a subject 110 (see FIG. 2; subject), and in the present embodiment, the magnetic resonance imaging apparatus 100 is a magnetic resonance imaging (MRI) apparatus that uses a nuclear magnetic resonance (NMR) phenomenon. FIG. 1 shows a tunnel bore type MRI apparatus comprising a cylindrical gantry, as an example of the magnetic resonance imaging apparatus 100. An apparatus body 101 includes a cylindrical tunnel 102 of which an axial direction is horizontal, and generates a static magnetic field in the tunnel 102 to form an imaging space. The apparatus body 101 is disposed in an electromagnetically shielded room, and a gradient magnetic field power supply 132, a sequencer 140, a high-frequency oscillator 151, a modulator 152, a high-frequency amplifier 153, a signal amplifier 162, a quadrature phase detector 163, an A/D converter 164, a controller 170, and the like (see FIG. 2) are disposed outside the electromagnetically shielded room and are electrically connected to the apparatus body 101 via a cable.

Configuration of Magnetic Resonance Imaging Apparatus

Figure 2:
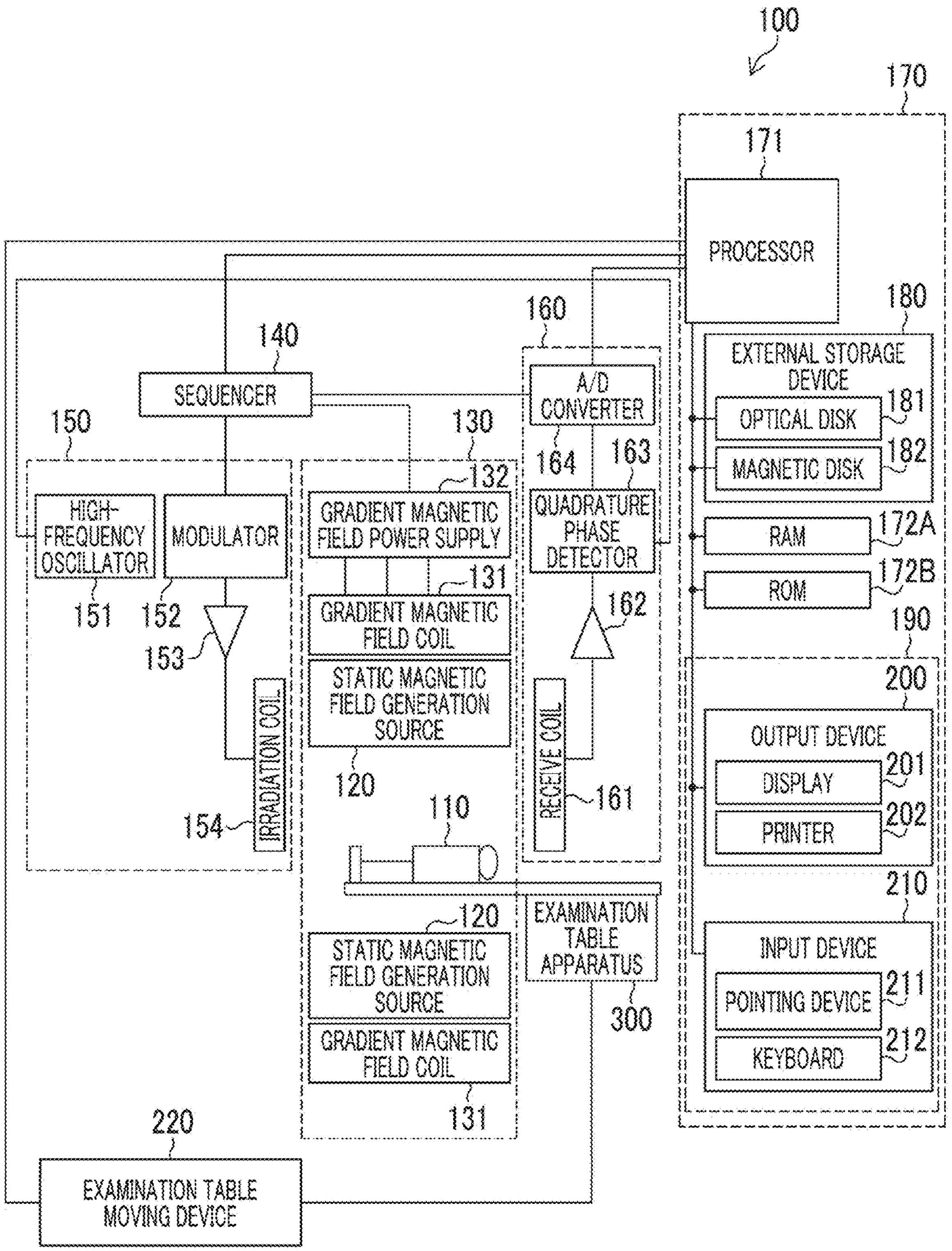
FIG. 2 is a diagram showing a configuration of a magnetic resonance imaging apparatus.

FIG. 2 is a diagram showing a configuration of the magnetic resonance imaging apparatus 100. As shown in FIG. 2, the magnetic resonance imaging apparatus 100 comprises a static magnetic field generation source 120, a gradient magnetic field generation unit 130, the sequencer 140, a high-frequency irradiation unit 150, a signal detection unit 160, and the controller 170.

The static magnetic field generation source 120 comprises a power supply and a superconducting coil (static magnetic field generation coil) (both of which are not shown), and generates a uniform static magnetic field in a static magnetic field space accommodating the subject 110 in a direction orthogonal to a body axis of the subject 110 in a case of a vertical magnetic field method, or in a body axis direction of the subject 110 in a case of a horizontal magnetic field method. The static magnetic field generation source 120 is disposed around the subject 110. The current and the voltage of the superconducting coil are measured by an ammeter and a voltmeter (not shown), and are input to a processor 171 (controller 170). It should be noted that the static magnetic field generation coil may be a normal conducting coil instead of the superconducting coil.

Returning to FIG. 2, the gradient magnetic field generation unit 130 includes gradient magnetic field coils 131 (gradient magnetic field generation coils) that generate gradient magnetic fields in three axial directions of X, Y, and Z, which are a coordinate system (stationary coordinate system) of the magnetic resonance imaging apparatus 100, and a gradient magnetic field power supply 132 that drives each of the gradient magnetic field coils 131, in a superimposed form in the static magnetic field space. Gradient magnetic fields Gx, Gy, and Gz are generated in the three axial directions of X, Y, and Z by driving the gradient magnetic field power supply 132 of each coil in response to an instruction, that is, control from the sequencer 140 described later. During imaging, a slice direction gradient magnetic field pulse (Gs) is applied in a direction orthogonal to a slice plane (imaging cross section) to set the slice plane with respect to the subject 110, and a phase encoding direction gradient magnetic field pulse (Gp) and a frequency encoding direction gradient magnetic field pulse (Gf) are applied in the remaining two directions orthogonal to the slice plane and orthogonal to each other to encode positional information in each direction in an echo signal.

The sequencer 140 repeatedly applies high-frequency magnetic field pulses (RF pulses) and gradient magnetic field pulses in a predetermined pulse sequence. The sequencer 140 operates based on the control of the processor 171 and transmits various instructions, that is, controls required for collection of data of the tomographic image of the subject 110 to the gradient magnetic field generation unit 130, the high-frequency irradiation unit 150, and the signal detection unit 160.

The high-frequency irradiation unit 150 irradiates the subject 110 with the RF pulse to cause nuclear magnetic resonance in the atomic nucleus spin of the atom constituting a biological tissue of the subject 110. The high-frequency irradiation unit 150 includes the high-frequency oscillator 151, the modulator 152, the high-frequency amplifier 153, and an irradiation coil 154 (high-frequency coil) that is a transmission-side high-frequency coil. The subject 110 is irradiated with electromagnetic waves by amplitude-modulating the RF pulse, which is output from the high-frequency oscillator 151, via the modulator 152 at a timing based on the instruction from the sequencer 140, amplifying the amplitude-modulated RF pulse via the high-frequency amplifier 153, and then supplying the amplified RF pulse to the irradiation coil 154 disposed near the subject 110.

The signal detection unit 160 detects the echo signal that is an NMR signal released by the nuclear magnetic resonance of the nuclear spins constituting the biological tissue of the subject 110. The signal detection unit 160 includes a receive coil 161 (high-frequency coil, RF receive coil; coil) that is a reception-side high-frequency coil, the signal amplifier 162, the quadrature phase detector 163, and the A/D converter 164 (analog/digital converter). The NMR signal as a response induced in the subject 110 by the electromagnetic waves applied from the irradiation coil 154 is detected by the receive coil 161 disposed near the subject 110, amplified by the signal amplifier 162, and then divided into signals of two systems orthogonal to each other by the quadrature phase detector 163 at the timing based on the instruction from the sequencer 140, and each of the signals is converted into a digital amount by the A/D converter 164 and then transmitted to the controller 170.

Configuration of Receive Coil

The receive coil 161 (coil) is configured as, for example, a unit comprising a plurality of receive coil elements and a receiver formed in a loop shape and disposed in a secondary element array shape, and receives a signal from the subject. The image of the subject is captured (reconstructed) by the signal received by the receive coil 161. In the magnetic resonance imaging system 10, as the receive coil 161, a coil for imaging various parts, such as a head, a spine, an abdomen, a leg, and an arm, can be used. The number of coils used in one imaging may be one or plural, and a plurality of coils (for example, a coil for a spine and a coil for abdomen) for imaging different parts may be used simultaneously.

An overall shape of the receive coil 161 is, for example, a blanket shape, a sheet shape, or a semi-cylindrical shape, and may be configured by combining a plurality of band-shaped members and the like. The cable is pulled out from an end part of such the blanket or the sheet. The number of cables may be one or plural depending on the imaging part or the like. A connector (not shown) of a cable end part is connected to a connector 322 provided on a top plate 310 (top plate).

Configuration of Controller

The controller 170 executes various types of data processing, displays the processing results, and stores the processing results. The controller 170 includes the processor 171, a storage device such as a random access memory (RAM) 172A and a read only memory (ROM) 172B, an external storage device 180 such as an optical disk 181 and a magnetic disk 182, and an input/output unit 190. In a case in which the signal detection unit 160 receives the signal or the data, the processor 171 executes processing such as signal processing and image reconstruction by using the RAM 172A as a work area, displays the tomographic image of the subject 110 as the result thereof on an output device 200, and records the tomographic image in the external storage device 180. In a case of executing these types of processing, the processor 171 can refer to a program or data recorded on the ROM 172B.

Under the control of the processor 171, the controller 170 can supply power a superconducting coil 124 (static magnetic field generation coil) from a power supply 122, and measure the supplied current and the voltage between current lead terminals of the superconducting coil 124 by using an ammeter 126 and a voltmeter 128. In addition, the controller 170 detects a magnetic body based on these measurement results to output the result.

The input/output unit 190 performs input and output of various control information of the magnetic resonance imaging apparatus 100 and control information of the processing executed by the controller 170, specifically, performs input, reception, and display of imaging parameters of the pulse sequence and the like. In addition, the input/output unit 190 receives an operation of issuing an instruction for the power supply to the static magnetic field generation coil, and outputs information indicating the power supply state or the measured voltage. The input/output unit 190 consists of an input device 210 including a pointing device 211 such as a trackball, a mouse, a pad, or a touch panel, and a keyboard 212, and an output device 200 including a display 201 such as a cathode-ray tube (CRT) or a liquid crystal display (LCD), and a printer 202. The input device 210 may be disposed near the output device 200, and, for example, an operator may interactively control the input device 210 while viewing the display 201, to instruct the magnetic resonance imaging apparatus 100 to execute various types of processing via the pointing device 211. In addition, the input operation may be performed by disposing the touch panel that operates as the input device 210 on a display surface of the display 201, and selecting or operating the display content of the display 201.

In addition, the input/output unit 190 may comprise an audio input/output device such as a microphone or a speaker, and this device allows the operator to perform an operation by audio via the microphone, or notification may be issued to the operator or the like by audio.

The subject 110 is placed on the top plate 310 of the examination table apparatus 300 and is accommodated in the static magnetic field space, which is the imaging space, by an examination table moving device 220 (see FIG. 2). The irradiation coil 154 on the transmission side and the gradient magnetic field coil 131 are installed in the static magnetic field space in which the subject 110 is accommodated, to face the subject 110 in a case of a vertical magnetic field method and to surround the subject 110 in a case of a horizontal magnetic field method. The receive coil 161 on the reception side is actually installed to face an imaging target part of the subject 110 or to surround the imaging target part. The receive coil 161 having a sheet shape may be laid on the top plate 310, the subject 110 may lie down on the sheet, and an end part of the sheet may be wound on the abdomen side (back side in a case in which the subject 110 is lying down in a prone state) for use. It should be noted that the subject may also be referred to as an examination subject.

It should be noted that, as the imaging target nuclide of the current MRI apparatus, a hydrogen atom nucleus (proton), which is a main constituent substance of the subject 110, is widely used in clinical practice. By visualizing information on a spatial distribution of a proton density or a spatial distribution of a relaxation time of an excited state, a morphology or a function of the human body, such as the head, the abdomen, or the limbs, is imaged two-dimensionally or three-dimensionally.

In the magnetic resonance imaging apparatus 100 according to the present embodiment, the processor 171 may include, for example, various processors as a hardware structure as follows. The "various processors" include, for example, a central processing unit (CPU) which is a general-purpose processor executing software (program) to function as various processing units, a programmable logic device (PLD), such as a field programmable gate array (FPGA), which is a processor of which a circuit configuration can be changed after manufacture, and a dedicated electric circuit, such as an application specific integrated circuit (ASIC), which is a processor of which a dedicated circuit configuration is designed to execute specific processing.

The processor 171 may be configured by one of these various processors, or may be configured by two or more processors of same type or different types (for example, a plurality of FPGAs or a combination of the CPU and the FPGA). Further, a plurality of processing units may be configured by one processor. As a first example the configuration of the plurality of processing units by one processor, there is a form in which one processor is configured by combining one or more CPUs and software, and this processor functions as the plurality of processing units, as represented by a computer, such as a client or a server. Second, there is a form in which a processor, which achieves the functions of the entire system including the plurality of processing units with one integrated circuit (IC) chip, is used, as represented by a system on chip (SoC) or the like. In this way, various processing units can be configured by one or more of the various processors described above, as the hardware structure.

The hardware structures of these various processors are, more specifically, an electric circuit (circuitry) in which the circuit elements, such as semiconductor elements, are combined. It should be noted that, in a case in which the various processors operate, a program or data recorded on a non-transitory tangible recording medium, such as the ROM 172B, can be referred to, and a recording medium, such as the RAM 172A, can be used as a transitory work area during the operation.

Configuration of Examination Table Apparatus

Figure 3:
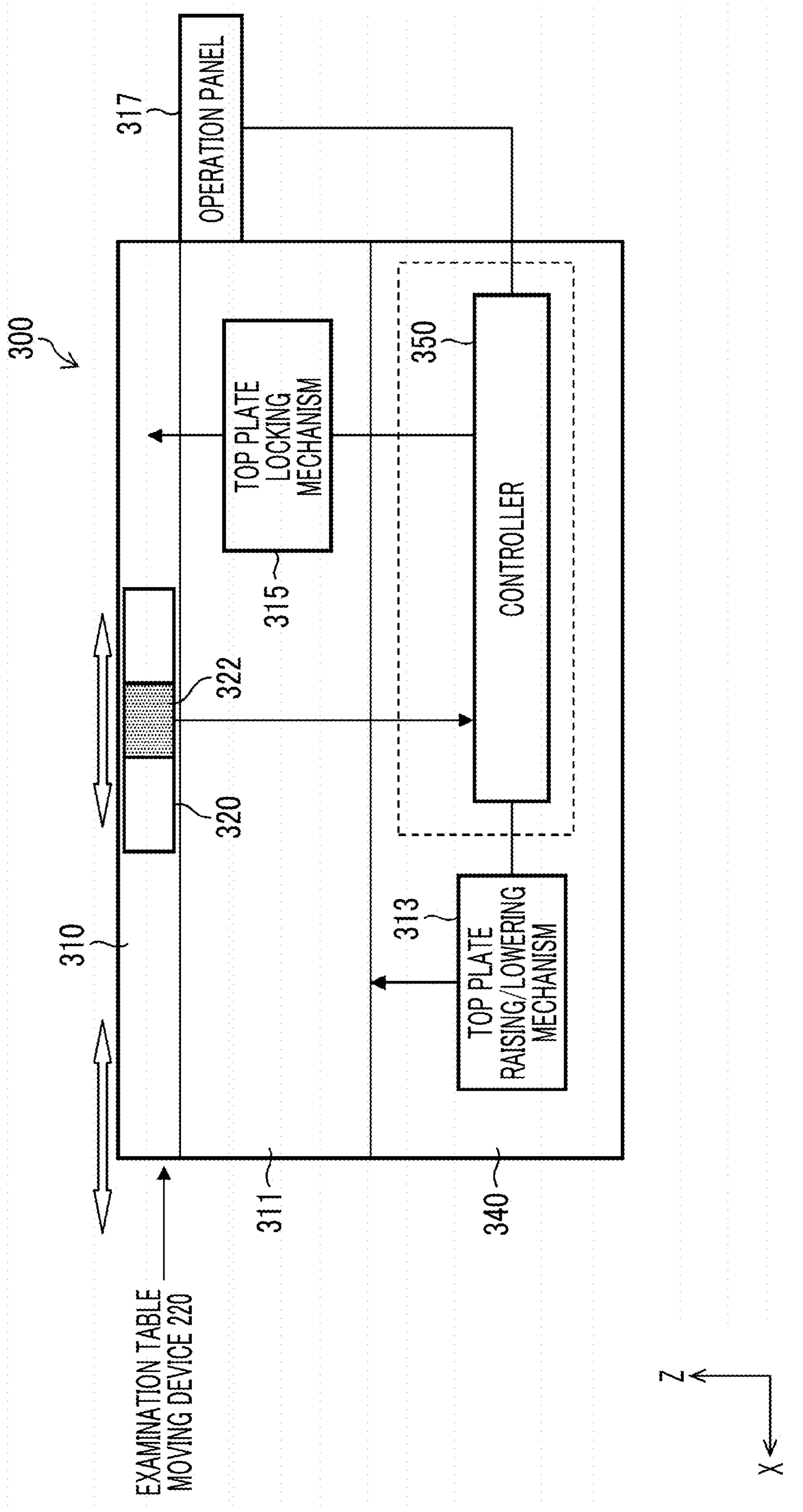
FIG. 3 is a diagram showing a configuration of an examination table apparatus according to the first embodiment.

FIG. 3 is a diagram showing a configuration of the examination table apparatus 300 (examination table apparatus) according to the first embodiment. As shown in FIG. 3, the examination table apparatus 300 includes the top plate 310 on which the subject 110 is placed, a top plate holding part 311, and a body part 340. Further, the examination table apparatus 300 comprises a controller 350 and an operation panel 317. It should be noted that, although an aspect is described in the first embodiment in which the examination table apparatus 300 is fixed to the apparatus body 101, the examination table apparatus 300 may be configured separately from the magnetic resonance imaging apparatus 100 so as to be connected to and separated from the apparatus body 101.

The top plate 310 is held by the top plate holding part 311 and is slidable to the inside or the outside of the imaging space by using the examination table moving device 220 (see FIG. 2) in the magnetic resonance imaging apparatus 100. In addition, the examination table apparatus 300 comprises a top plate lock mechanism 315, and the top plate lock mechanism 315 can lock the top plate 310 not to be slidable, or unlock the top plate 310 to be slidable. The top plate locking/unlocking can be realized by inserting and pulling out a locking pin into and from the top plate 310, or by attracting and attraction-releasing a magnet on the top plate 310 side by using an electromagnet. Further, the examination table apparatus 300 comprises a top plate raising/lowering mechanism 313 (for example, can be configured by an oil pressure jack, a pantograph, or the like), and the top plate 310 and the top plate holding part 311 can be raised and lowered.

The user can perform, via the operation panel 317, an operation of locking the top plate 310 or an operation of sliding the top plate 310. Information such as a locking state or a sliding state of the top plate 310, a connection state of the connector 322, or the like may be displayed on the operation panel 317.

A plurality of openings 320 are provided in the top plate 310, and the connector 322 is slidable (movable) in the openings 320. A detailed configuration and a sliding aspect of the connector 322 will be described later.

Configuration of Controller

Figure 4:
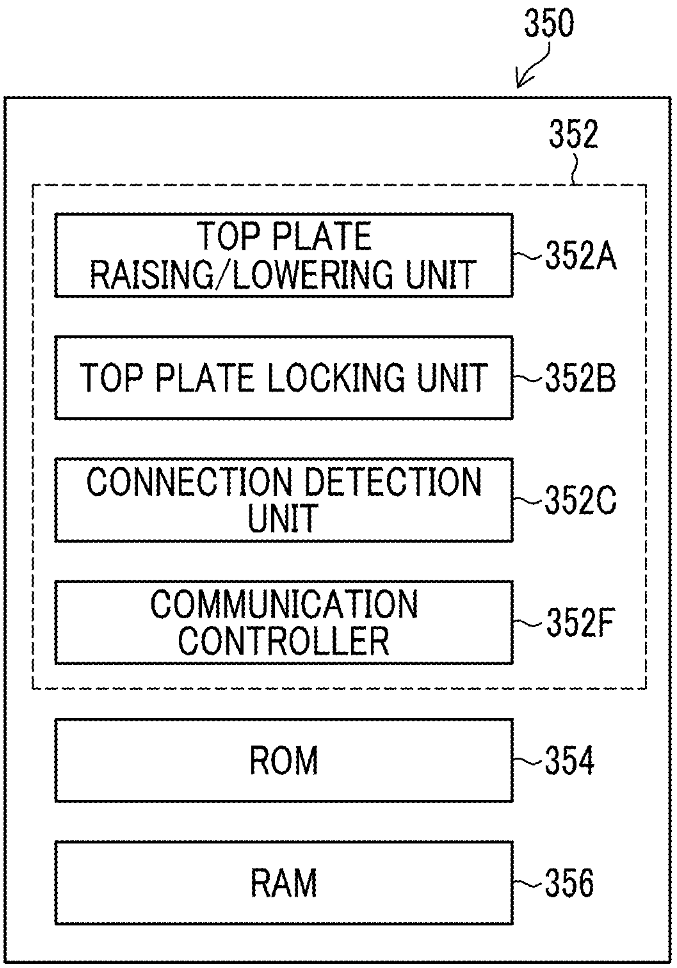
FIG. 4 is a diagram showing a configuration of a controller of the examination table apparatus.

FIG. 4 is a diagram showing a configuration of a controller 350 of the examination table apparatus 300 according to the first embodiment. As shown in FIG. 4, the controller 350 comprises a processor 352, a read only memory (ROM) 354, and a random access memory (RAM) 356. The processor 352 can be configured by various processors in the same manner as in the processor 171. In a case in which these various processors operate, a program or data recorded on a non-transitory and tangible recording medium, such as the ROM 354, can be referred to, and a recording medium, such as the RAM 356, can be used as a transitory work area during the operation.

Function of Processor

The processor 352 has, as functions thereof, a top plate raising/lowering unit 352A, a top plate locking unit 352B, a connection detection unit 352C, and a communication controller 352F. The top plate raising/lowering unit 352A controls the top plate raising/lowering mechanism 313 to raise and lower the top plate 310 and the top plate holding part 311, and the top plate locking unit 352B controls the top plate lock mechanism 315 to lock and unlock the top plate 310. The connection detection unit 352C detects that the cable of the coil is connected to or disconnected from the connector 322, and the communication controller 352F acquires the signal received by the receive coil 161 (coil) via the connector 322 and transmits the acquired signal to the apparatus body 101.

Disposition of Connector

Figure 5:
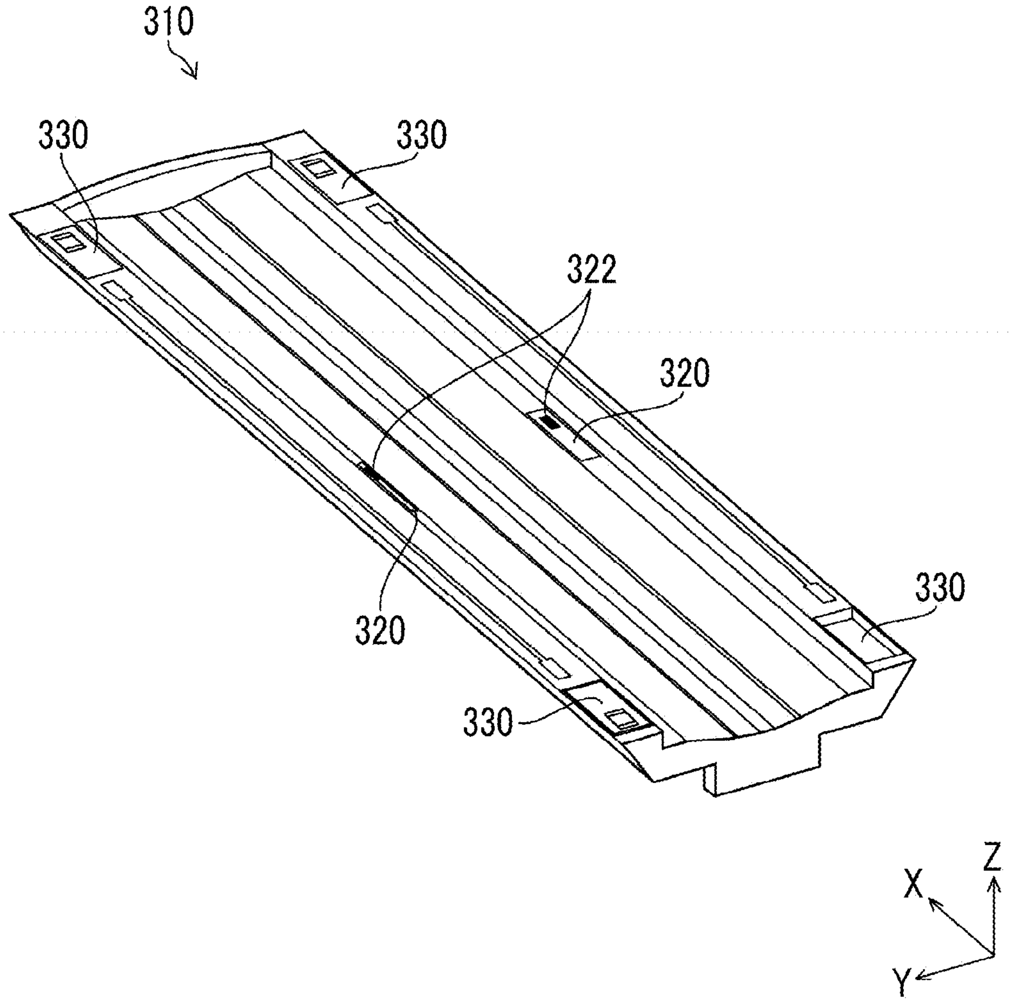
FIG. 5 is a perspective view showing a disposition example of a connector on a top plate.

FIG. 5 is a perspective view showing a disposition example of the connector on the top plate 310. In the example shown in FIG. 5, a plurality of connectors 322 (connectors) are provided on both sides (+Y side and −Y side) of the top plate 310 in a lateral direction, with one connector 322 on each side. A plurality of openings 320 (a plurality of openings) corresponding to the connectors 322 are provided in the top plate 310, and the connector 322 is slidable with respect to the top plate 310 in a part (a range of the openings 320) of the top plate 310 in a longitudinal direction (±X direction). It should be noted that grooves (one groove corresponding to one connector; a plurality of grooves as a whole) may be provided instead of the openings 320. The groove need not penetrate in the Z direction. In addition, the plurality of connectors 322 may be provided on both sides of the top plate 310 in the lateral direction (see FIGS. 13A and 13B described later). The plurality of connectors 322 are slidable independently of each other. Further, the top plate 310 is provided with a total of four fixed connectors 330 on both end parts (+X side and −X side) in the longitudinal direction, on both sides in the lateral direction.

Figure 6:
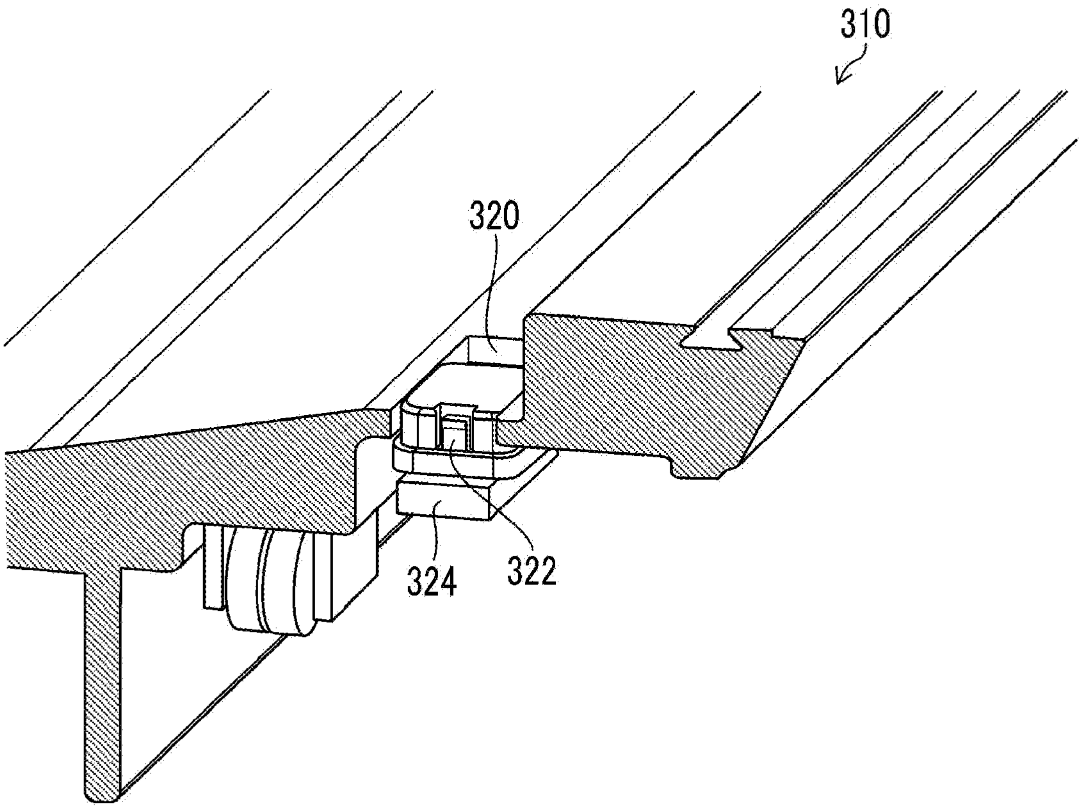
FIG. 6 is a cross-sectional view of the top plate in a connector portion.

FIG. 6 is a cross-sectional view of the top plate 310 in a portion of the connector 322. As shown in FIG. 6, a support member 324 (a plurality of support members) that supports the connector 322 is provided. The support member 324 is provided corresponding to each of the plurality of connectors 322 (in the example of FIG. 5, one each in the ±Y direction), and the plurality of support members 324 are provided in total.

Configuration of Sliding Mechanism

Figure 7:
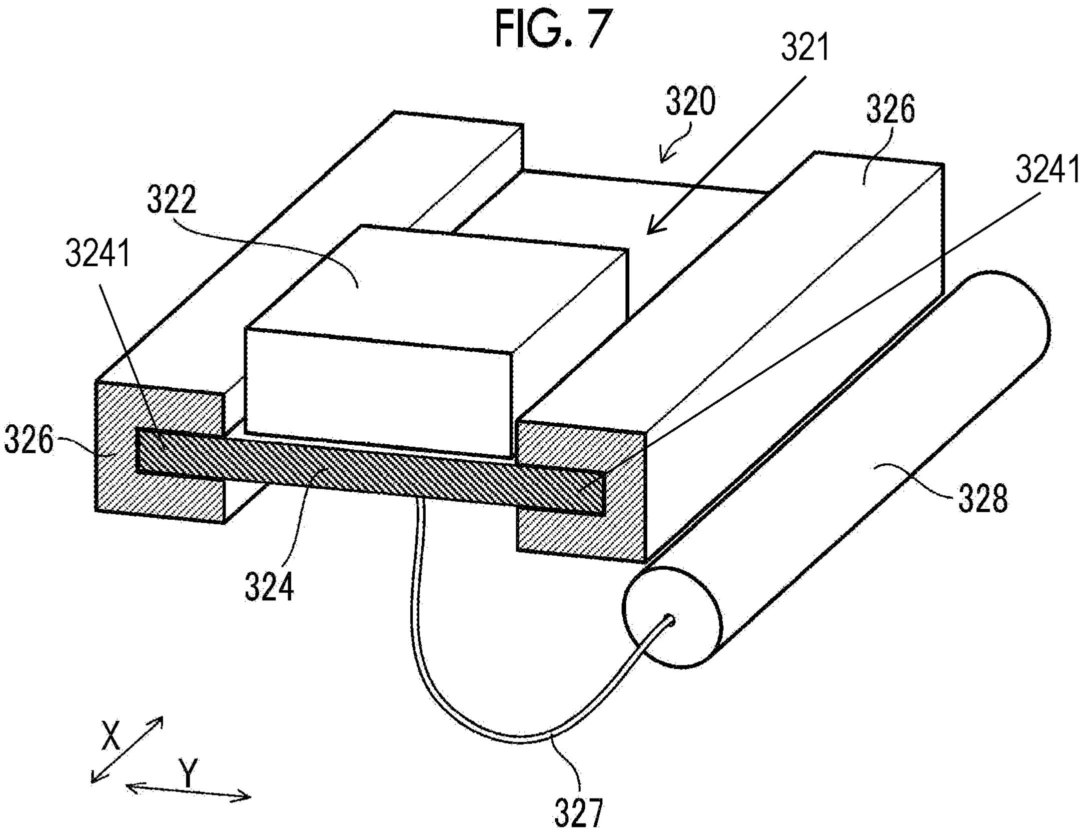
FIG. 7 is a diagram showing a configuration example of a sliding mechanism.

FIG. 7 is a diagram showing a configuration example of a mechanism (sliding mechanism) for sliding the connector 322. In the example of FIG. 7, a holding member 326 (plurality of holding members) holds a horizontal-direction end part 3241 (±Y side) of the support member 324, and the holding member 326 is disposed on both sides (±Y side) of the top plate 310 in the lateral direction and projected in the longitudinal direction (±X side), and is fixed to the top plate 310. Therefore, the plurality of holding members are provided on the entire top plate 310. The support member 324 slides with respect to the holding member 326, whereby each of the connectors 322 slides with respect to the top plate 310 in the ±X direction. In the first embodiment, it is possible for the user to slide the connector 322.

In addition, the cable 327 is pulled out from the connector 322, and the cable 327 is connected to the balun 328. The "balun" is an element for converting electrical signals in a balanced state and in an unbalanced state.

Figure 8A:
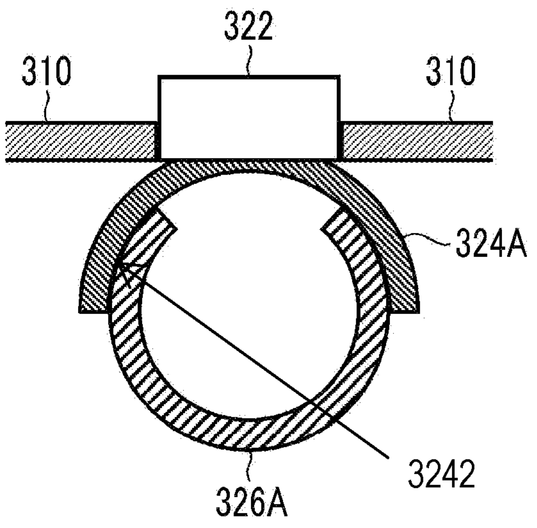
FIGS. 8A and 8B are diagrams showing another configuration example of the sliding mechanism.
Figure 8B:
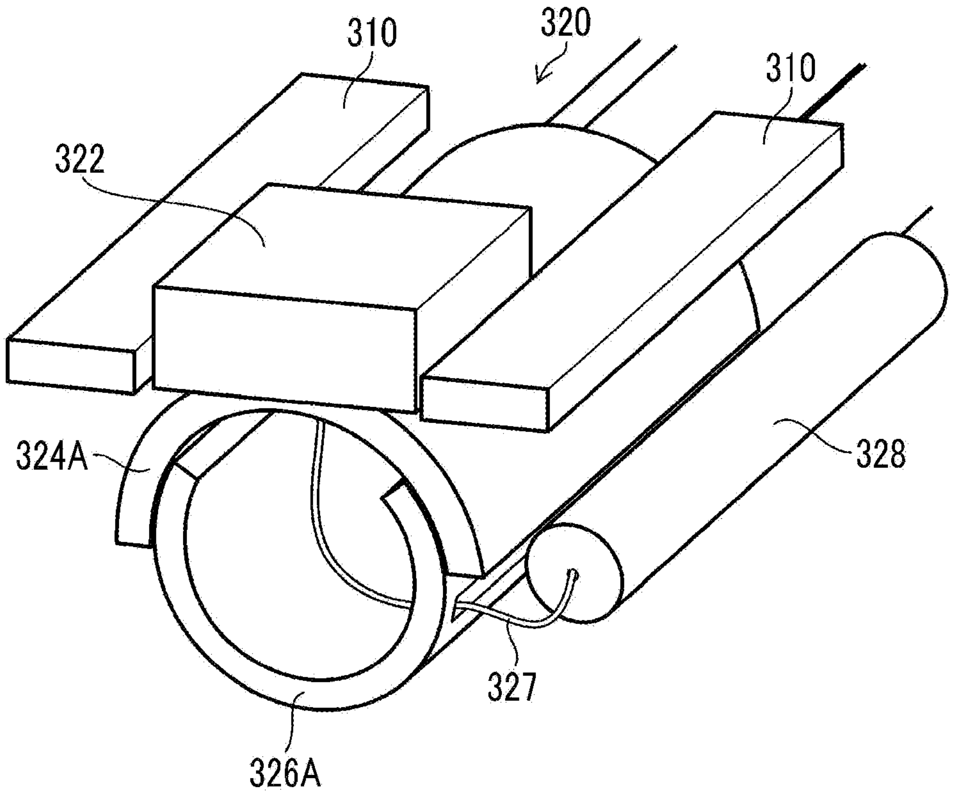

FIGS. 8A and 8B are diagrams showing another configuration example of the sliding mechanism. In the examples of FIGS. 8A and 8B, the connector 322 is exposed from the opening 320 formed in the top plate 310. As shown in FIG. 8A, a support member 324A (guide) that supports the connector 322 has a semicircular cross section, and a holding member 326A is a cylindrical shape (tubular member) with an open top. The holding member 326A holds at least a part of a vertical-direction lower surface 3242 of the support member 324A. The holding member 326A is disposed on both sides (±Y side) of the top plate 310 in the lateral direction and projected in the longitudinal direction (±X side), and is fixed to the top plate 310. Therefore, the plurality of holding members are provided in total. The support member 324A slides with respect to the holding member 326A, whereby each of the connectors 322 slides with respect to the top plate 310 in the ±X direction (see FIG. 8B). As in the example of FIG. 7, the cable 327 is pulled out from the connector 322, and the cable 327 is connected to the balun 328.

Configuration for Shielding Gap

In the example of FIG. 7 described above, a gap 321 between the connector 322 and the opening 320 is shielded by the support member 324, and in the examples of FIGS. 8A and 8B, a gap is shielded by at least the support member 324A, and a hole does not penetrate in the Z direction. As a result, the pinching of the body (fingers or the like) of the user or the subject, the spilling of the liquid, the dropping of the article, and the like can be prevented.

Figure 9:
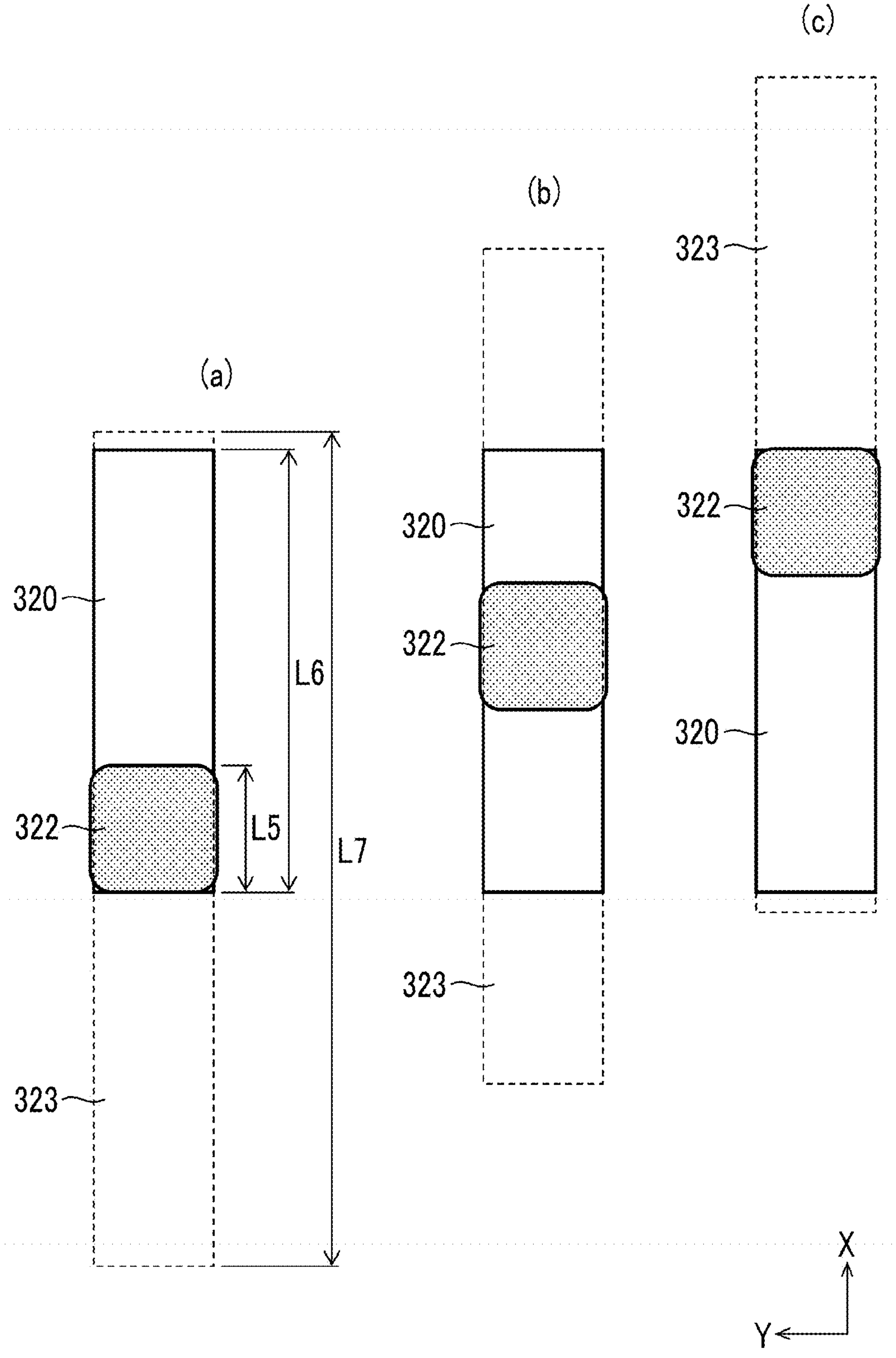
FIG. 9 is a schematic diagram showing a configuration for shielding a gap between the connector and an opening.

FIG. 9 is a schematic diagram showing a configuration (a state in which a connector portion is viewed from the +Z direction) for shielding the gap. A part (a) to a part (c) of FIG. 9 show a state in which the connector 322 is located at the −X side end part, the center, and the +X side of the opening 320, respectively. In the example shown in FIG. 9, a length of the connector 322, a length of the opening 320, and a length of the support member 323 in the X direction are L5, L6, and L7, respectively. As is clear from FIG. 9, by making the support member 323 sufficiently long, the opening (hole) does not penetrate in the Z direction even in a case in which the connector 322 is slid. Specifically, it is sufficient that $L7 \geq (L6-L5)\times 2+L5=L6\times 2-L5$ (it is also necessary that a relationship of a width of the support member 323 in the Y direction ≥a width of the opening 320 in the Y direction is satisfied). It should be noted that, since the gap need only be shielded by at least one of the support member or the holding member, the opening 320 may be shielded by making the holding member long (wide).

Variation of Sliding Mechanism

FIGS. 10A to 10F are diagrams showing a variation of the sliding mechanism. In a sliding mechanism 500 shown in FIG. 10A, one end of an arm 508 is rotatably fixed to a circular plate member 510, and the other end slides in a range of an opening 504 formed inside a frame member 502. The connector is provided on the support member 506 provided at the other end, so that the connector can be slid.

Figure 10A:
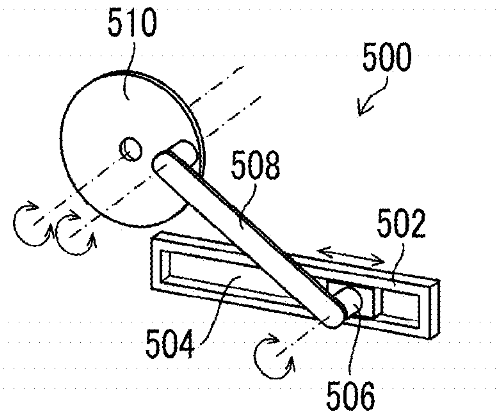
Figure 10B:
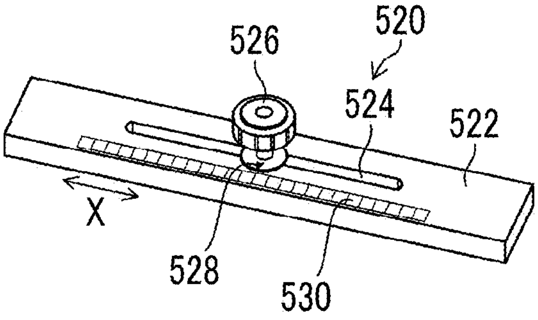
Figure 10B:
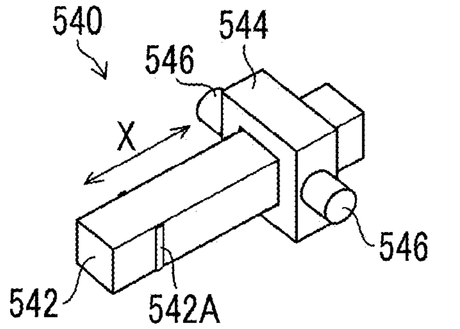
Figure 10B:
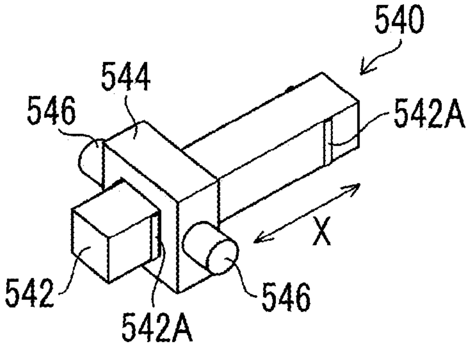

In a sliding mechanism 520 shown in FIG. 10B, an opening 524 is formed in a plate-shaped member 522 fixed to the top plate 310, and a shaft member (not shown) slides in a range of the opening 524. A rotatable knob 526 is formed on the shaft member, and the shaft member can be allowed to slide or prevented from sliding by rotating the knob 526 to tighten or loosen the knob 526. The connector can be slid by fixing the connector to the knob 526. In addition, since a pointing 528 is formed on the shaft member and slides along with the shaft member, and a scale 530 is formed on the plate-shaped member 522, the sliding position of the connector can be understood. Such an index or scale may be provided in the sliding mechanism of the above-described aspect and the sliding mechanism of another aspect described later, so that the sliding position of the connector can be understood.

In a sliding mechanism 540 shown in FIG. 10C1, a frame member 544 is fitted to a square bar-shaped shaft member 542 that is projected in the ±X direction and fixed to the top plate 310, and the frame member 544 is slidable with respect to the shaft member 542. FIG. 10C2 shows a state in which the frame member 544 is slid to the side opposite to the side in FIG. 10C1. In addition, a protruding portion 542A can be provided at both ends of the sliding range, and the frame member 544 can be prevented from sliding beyond the sliding range. Further, a fixing member 546 is provided on the frame member 544 in the Y direction, and the frame member 544 can be allowed to slide or be prevented from sliding by screwing or loosening the fixing member 546. The connector can be slid by fixing the connector to the frame member 544 as described above. In this sliding mechanism 540 as well, the opening (not shown) is formed in a part of the top plate 310 in the longitudinal direction (±X direction), as in other aspects, so that the movement range of the connector can be restricted (the same applies to sliding mechanisms 550 and 560 described later).

Figure 10D:
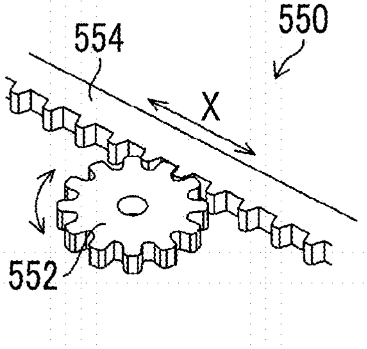

In the sliding mechanism 550 shown in FIG. 10D, a pinion 552 (fixed to the top plate 310) and a rack 554 are engaged with each other, and the user can rotate the pinion 552 (or a dial or the like in conjunction with the pinion 552) to parallel-translate the rack 554. Therefore, it is possible to slide the connector (not shown) by fixing the connector to the rack 554.

Figure 10E:
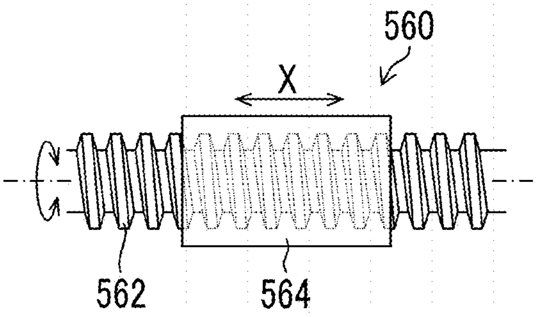

In the sliding mechanism 560 shown in FIG. 10E, a ball screw 562 projected in the longitudinal direction of the top plate 310 is rotated by a dial or a handle (not shown), whereby a nut 564 is caused to perform linear movement. Therefore, it is possible to slide the connector by fixing the connector to the nut 564.

Figure 10F:
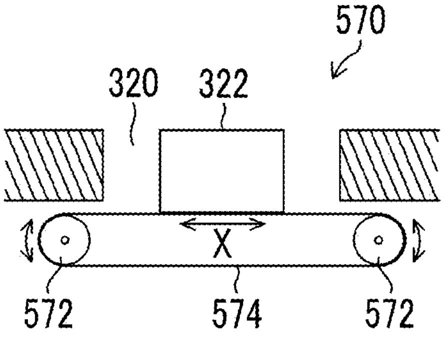

In the sliding mechanism 570 shown in FIG. 10F, two shaft members 572 that rotate around the Y axis are provided in the X direction, and a belt 574 is wound around the peripheries of the shaft members 572. The shaft member 572 is rotated by a dial or a handle (not shown), whereby the belt 574 is transported in the X direction. Therefore, it is possible to slide the connector 322 by fixing the connector 322 to the belt 574.

It should be noted that, also in the sliding mechanism of the aspects shown in FIGS. 10A to 10F, it is preferable to shield the gap between the connector and the opening as in the description with reference to FIG. 9 and the like.

Figure 11:
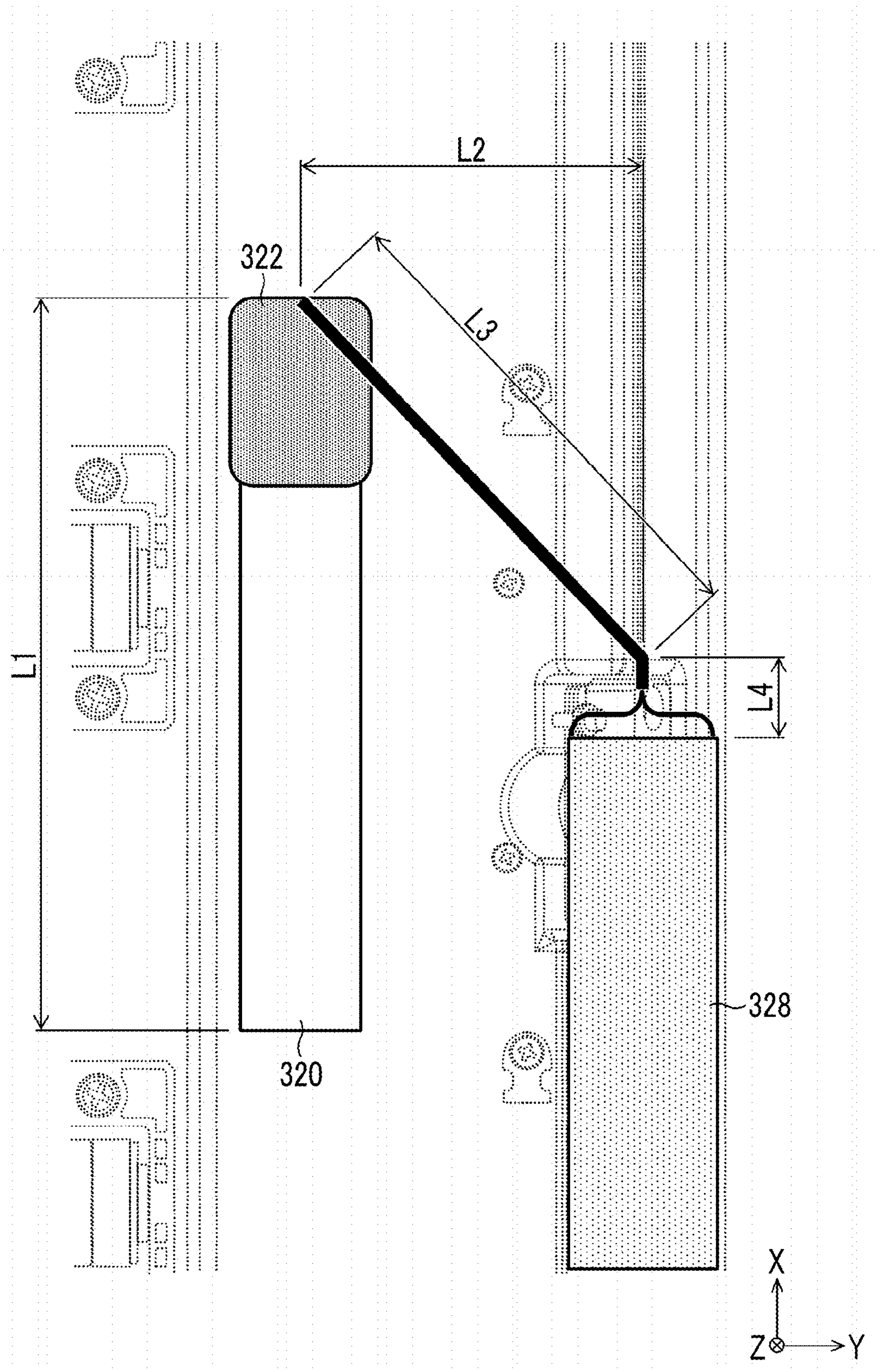
FIG. 11 is a diagram showing a cable length required for the connector.

FIG. 11 is a diagram (a state in which the top plate 310 is viewed from the −Z side) showing the cable length required for the connector. In a case in which a bending point of the cable 327 is located at the center of the movable range (length L1) of the connector 322, a Y-direction distance from the center of the connector 322 to the center of the balun 328 is denoted by L2 and an X-direction length from the bending point of the cable 327 to the balun 328 is denoted by L4, $L3=\{(L1/2)^2+L2^2\}^{1/2}$ and the total cable length=L3+L4. For example, in a case in which L1=200 mm, L2=90 mm, and L4=30 mm, L3 is approximately 135 mm, and the total cable length is approximately 165 mm, in a case in which L1=400 mm, the total cable length is approximately 255 mm, and in a case in which L1=600, the total cable length is approximately 315 mm.

Connection Pattern of Cable

Figure 12C:
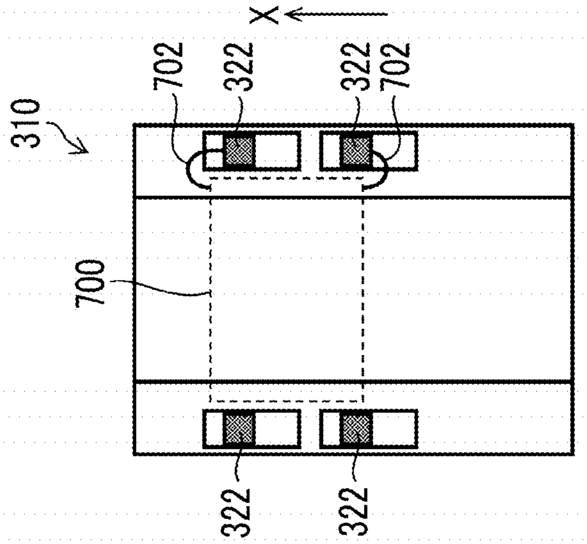
FIGS. 12A to 12C are diagrams showing a state in which a cable of a coil is connected to the connector.
Figure 12B:
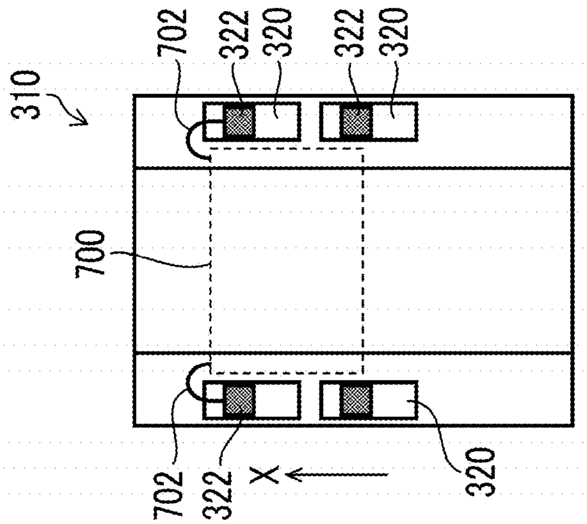
Figure 12A:
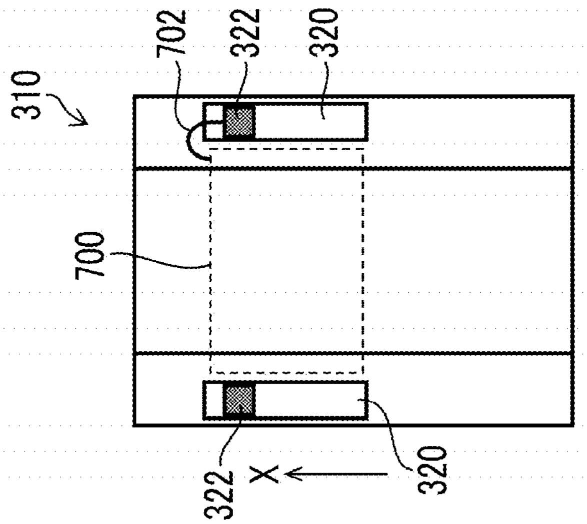

FIGS. 12A to 12C are schematic diagrams showing a pattern (variation of the number of cables, a position of a connected connector, and the like) in which the cable of the coil is connected to the connector. In the example shown in FIG. 12A, one cable 702 of a coil 700 is connected to the connector 322 on one side (any one of the ±Y side). It should be noted that the coil 700 can be a coil for imaging a specific part of the subject, for example, a coil for a spine imaging, but may be another part (the same applies to other aspects). In the example shown in FIG. 12B, two cables 702 of the coil 700 are connected to the connectors 322 on both sides. In this way, in the first embodiment, the coil for imaging the specific part of the subject is connectable to one connector provided on one side (+Y side) of the top plate 310 in the lateral direction (±Y direction) among the plurality of connectors 322, and the other connector provided on the other side (−Y side) of the top plate 310 in the lateral direction among the plurality of connectors 322. In the example shown in FIG. 12C, there are two cables 702 of the coil 700, and the two cables 702 are connected to the connector 322 on the same side (the −Y side in the same portion).

As described above, according to the first embodiment, an appropriate connection pattern can be selected in accordance with the imaging part or the configuration of the coil (the number of cables, the cable pull-out position, and the like).

Slidable Range of Connector

Figure 13A:
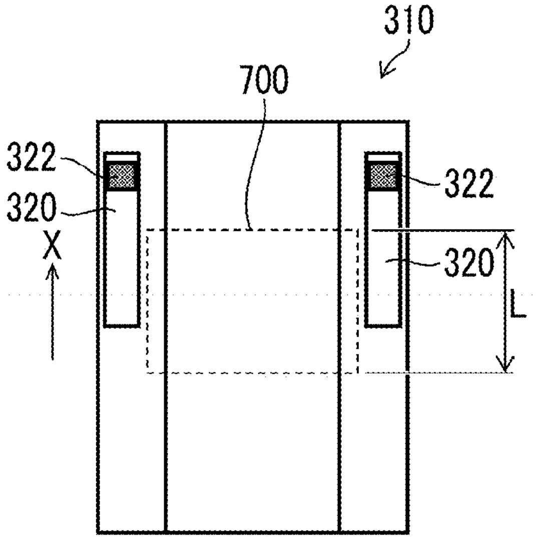
FIGS. 13A and 13B are schematic diagrams showing that the connector is movable in a range overlapping the coil.
Figure 13B:
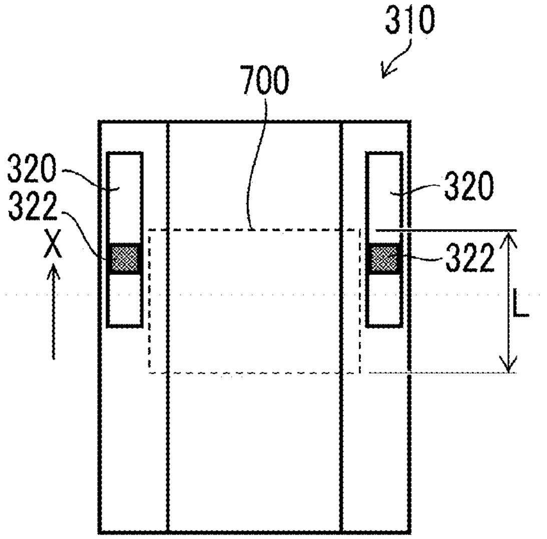

FIGS. 13A and 13B are schematic diagrams showing a slidable range of the connector. The X-direction length of the connector 322 is slidable within a range of the opening 320, and the coil 700 (coil for the specific part described above, for example, a coil for a spine may be used) is L. In the aspect shown in FIGS. 13A and 13B, in a case in which the subject in a state in which the coil 700 is attached is placed on the top plate 310, the connector 322 is slidable to a position overlapping a range (range of the length L) in which the coil 700 is present in the longitudinal direction (±X direction) of the top plate 310. According to such an aspect, it is possible to shorten the cable routing. It should be noted that such a sliding can be realized by determining the dimension of the opening 320 in accordance with the dimension and the cable length of the coil expected to be used. In addition to the above-described aspect, in the present invention, for example, an aspect can be considered in which the cable is eliminated in the spine coil (coil for a spine). That is, an aspect is also considered in which the cable is hidden inside the spine coil and only the connector is exposed to the exterior.

Figure 14:
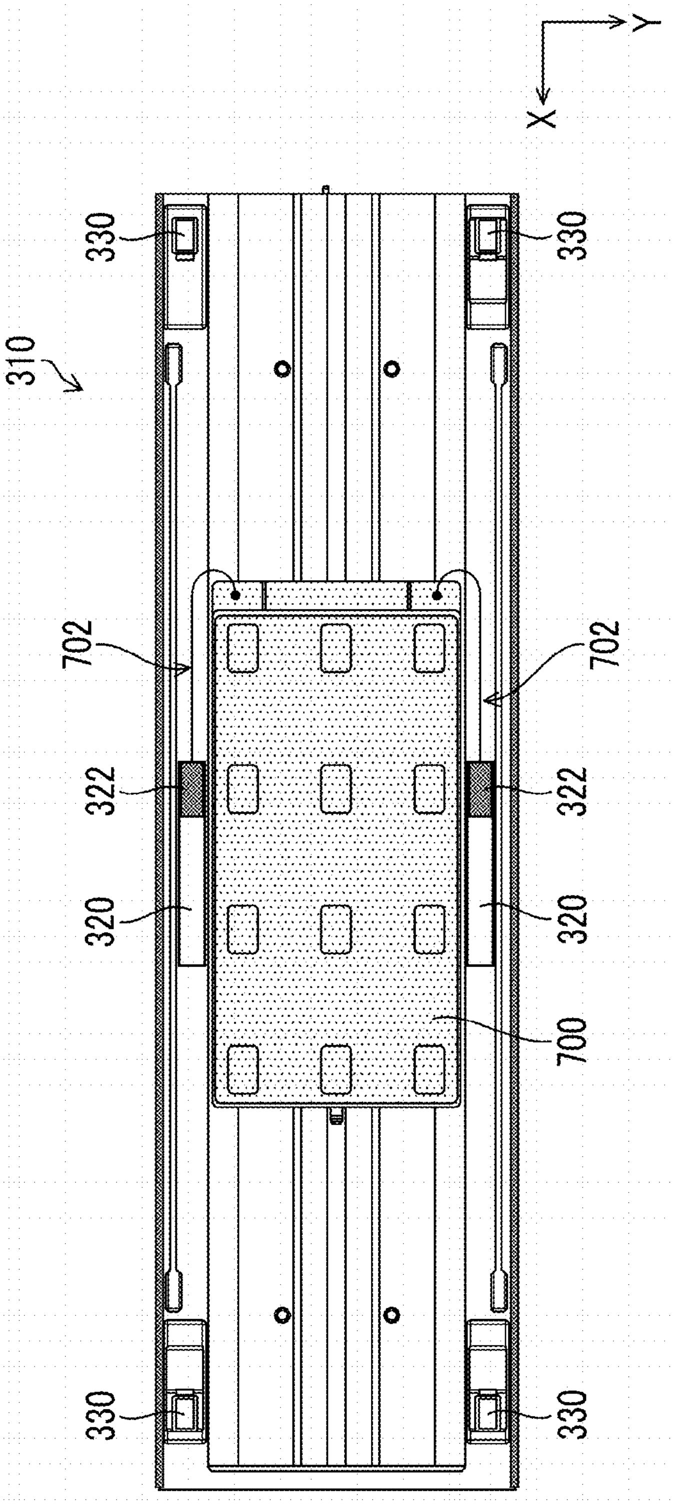
FIG. 14 is a diagram showing a state in which a coil for a spine is connected to the connector.

FIG. 14 is a diagram showing a state in which the coil 700 for a spine is connected to the connectors 322 on both sides in the Y direction. The connector 322 is slid to the "position overlapping a range in which the coil 700 is present in the longitudinal direction of the top plate 310 in a case in which the subject in a state in which the coil 700 is attached is placed on the top plate 310".

Connection of Coil for Imaging Different Parts

Figure 15:
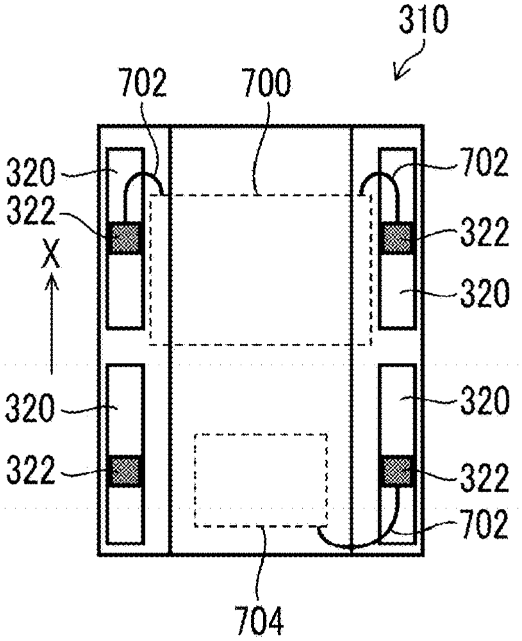
FIG. 15 is a diagram showing a state in which coils for imaging different parts of a subject are connected to the connector.

FIG. 15 is a schematic diagram showing a state in which the plurality of coils are connected to the connector. In the example of FIG. 15, the coil 700 is connected to the connector 322 on the +X side (on the ±Y side; both sides in the lateral direction), and a coil 704 is connected to the connector 322 on the −X side (on the −Y side in the example shown). The coil 700 is, for example, a coil for a spine imaging, and the coil 704 is, for example, a coil for leg imaging. That is, according to the first embodiment, the coils for imaging different parts of the subject can be connected to one connector and the other connector among the plurality of connectors 322.

Variation of Connector Disposition

Figure 16:
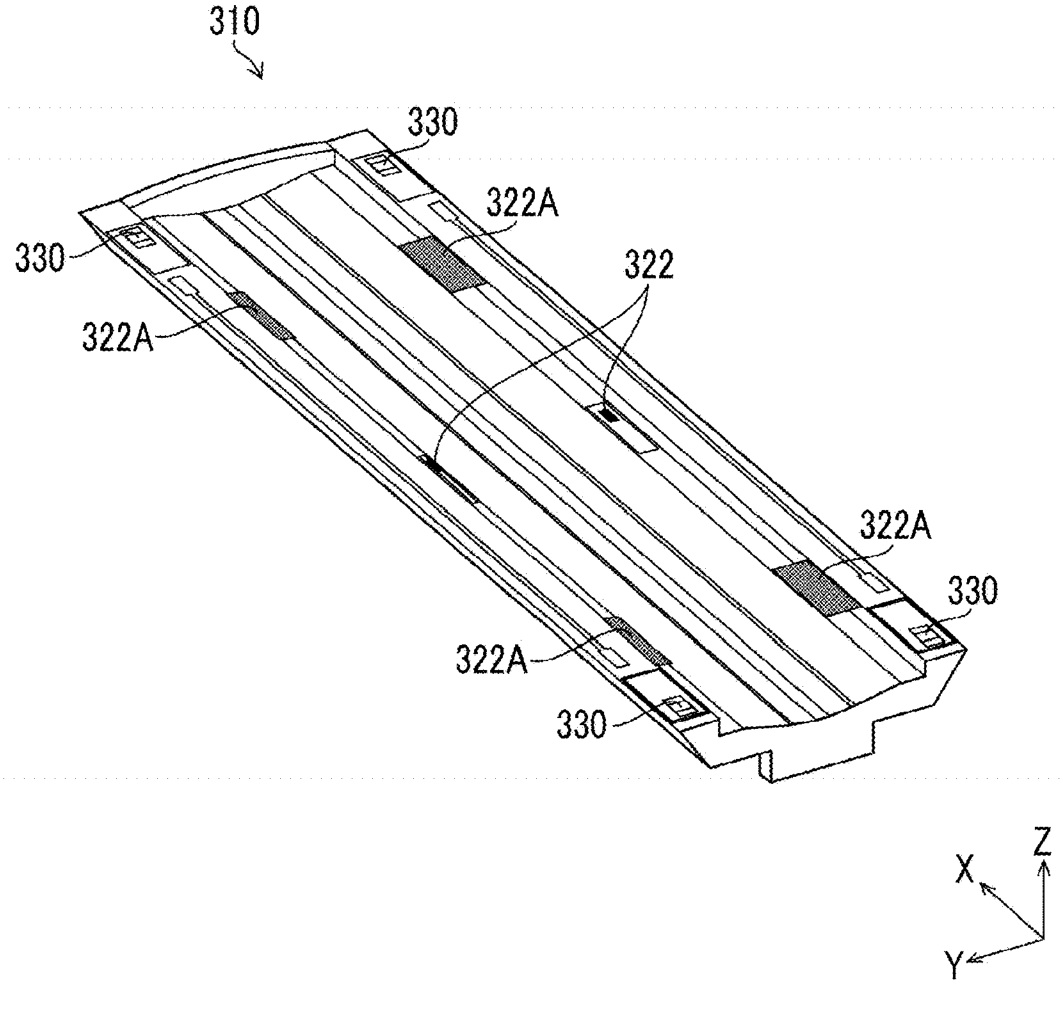
FIG. 16 is a diagram showing an aspect in which the connector is additionally disposed.

FIG. 16 is a perspective view showing a variation of the connector disposition. In the example shown in FIG. 16, as in the example of FIG. 5, the slidable connectors 322 are disposed on both sides (±Y side) in the lateral direction in the vicinity of the center of the top plate 310 in the X direction, and a slidable connectors 322A are disposed on both sides of the lateral direction at the +X side end part and the −X side end part of the top plate 310. The configurations of the connector 322A (the connector slides within the range of the opening, the support member and the holding member are provided, and the like) are the same as the configurations of the connector 322. It should be noted that, in the example of FIG. 16, as in the example of FIG. 5, a total of four fixed connectors 330 are disposed.

As described above, with the examination table apparatus 300 and the magnetic resonance imaging system 10 according to the first embodiment, it is possible to handle the connection of a wide variety of coils while shortening the cable length.

Second Embodiment

An examination table apparatus and a magnetic resonance imaging system according to the second embodiment of the present invention will be described. The second embodiment is different from the first embodiment in that the controller controls the sliding mechanism to slide the connector.

Figure 17:
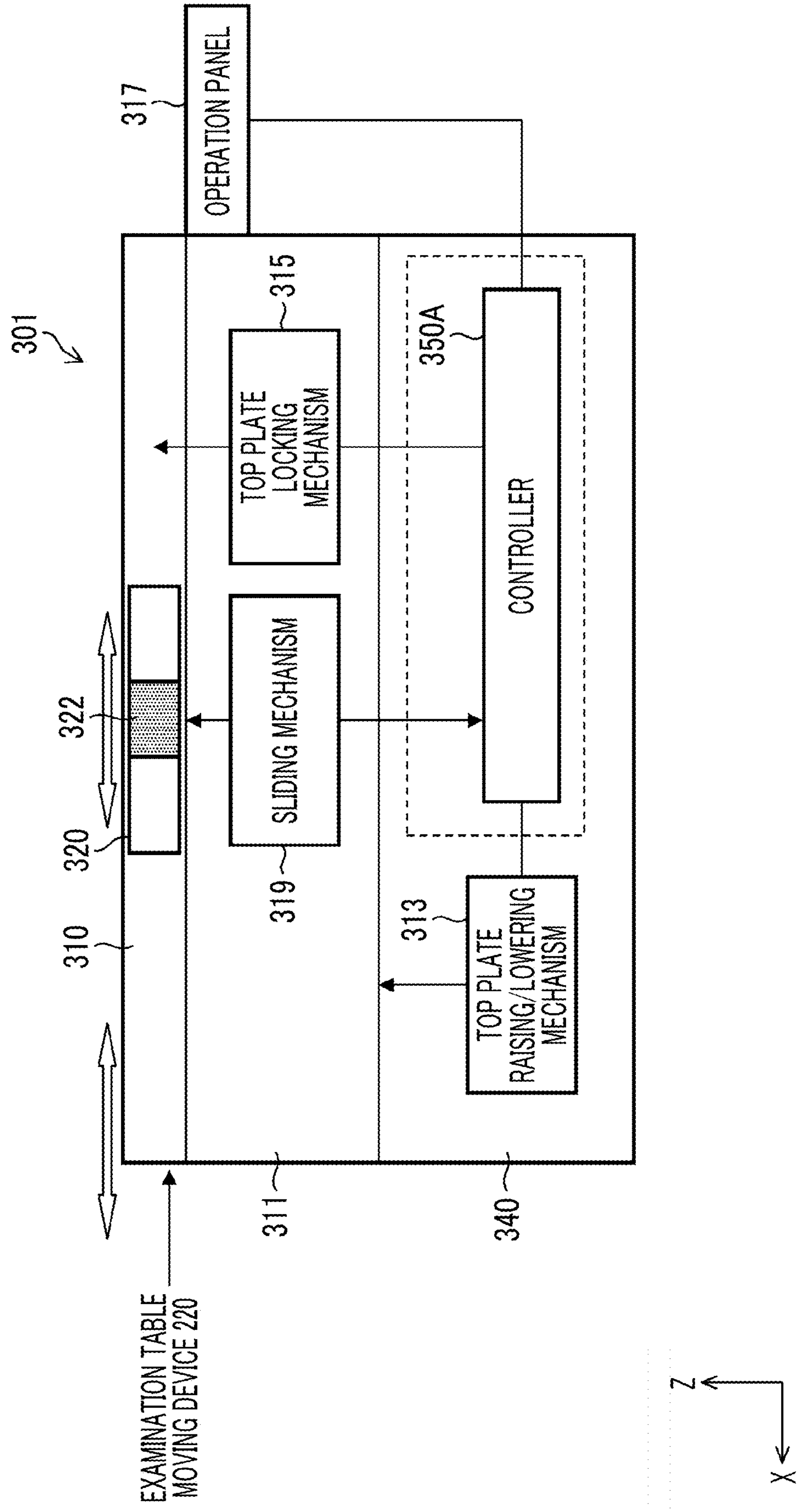
FIG. 17 is a diagram showing a configuration of an examination table apparatus according to a second embodiment.

FIG. 17 is a diagram showing a configuration of an examination table apparatus 301 according to the second embodiment. The examination table apparatus 301 comprises a connector sliding mechanism 319 (sliding mechanism), and a controller 350A (processor) controls the sliding mechanism to slide the connector.

Figure 18:
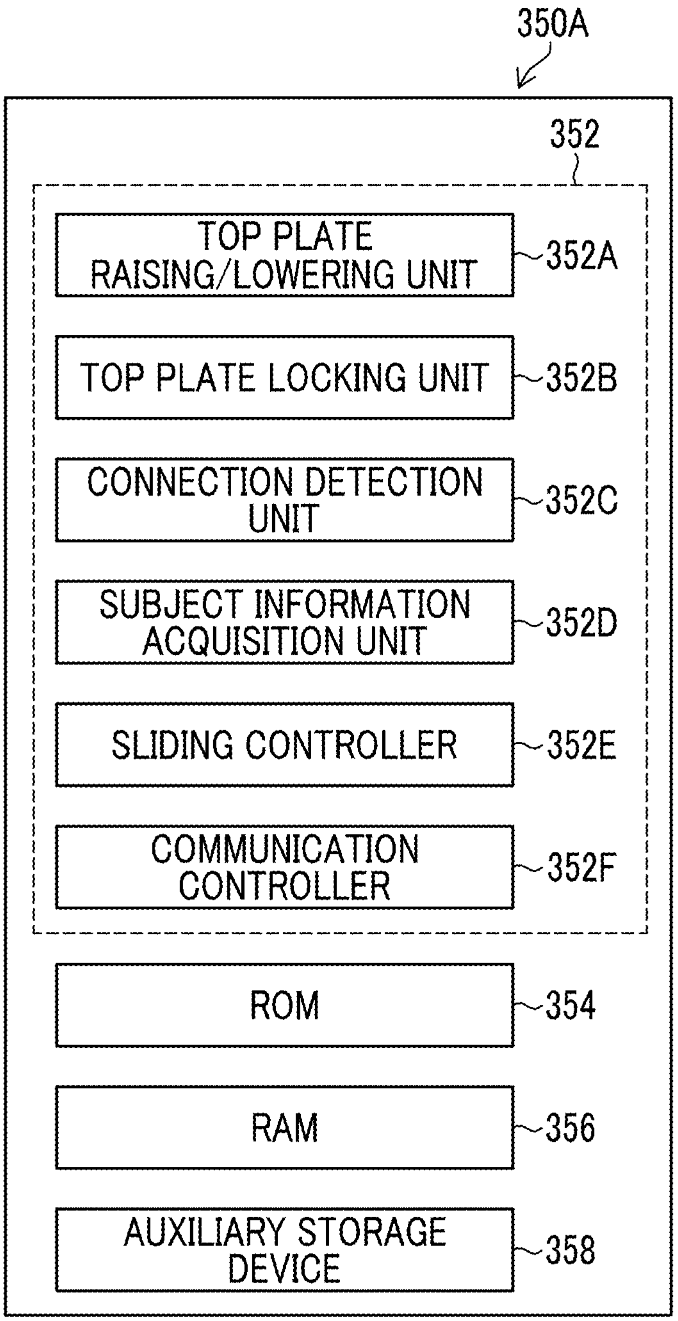
FIG. 18 is a diagram showing a configuration of a controller according to the second embodiment.

FIG. 18 is a diagram showing a configuration of the controller 350A according to the second embodiment. The controller 350A has functions of a subject information acquisition unit 352D and a sliding controller 352E in addition to the function of the controller 350 according to the first embodiment. These functions can be realized by performing processing using software by various processors or electric circuits, like other functions. The controller 350A comprises an auxiliary storage device 358. The auxiliary storage device 358A is configured by using various optical magnetic storage devices, semiconductor memories, and the like, and can store information on the coil or the connector (an imaging part, a cable length, and a slidable range of the connector), information on the subject, and the like. Since the other configurations of the controller 350A are the same as the configurations of the controller 350, the detailed description thereof will not be repeated.

Configuration, Disposition, and Sliding Mechanism of Connector

In the second embodiment as well, the same connector configuration, disposition, and sliding mechanism as in the first embodiment can be adopted. Specifically, the plurality of connectors are provided on both sides (±Y direction) of the top plate 310 in the lateral direction, with one or more connectors on each side, and the connectors are slidable with respect to the top plate 310 in a range of the openings in a part of the top plate 310 in the longitudinal direction (±X direction). In addition, the same sliding mechanism as that shown in FIGS. 7, FIGS. 8A and 8B, and FIGS. 10A to 10F can be adopted, and in these sliding mechanisms, the connector 322 can be slid with respect to the top plate 310 by rotating or translating members such as a dial, a gear, a ball screw, a shaft member, via a motor, for example, by using the controller 350A (processor) and transmitting the rotation or translation force to the connector, the support member, or the holding member.

Sliding Control of Connector

Figure 19:
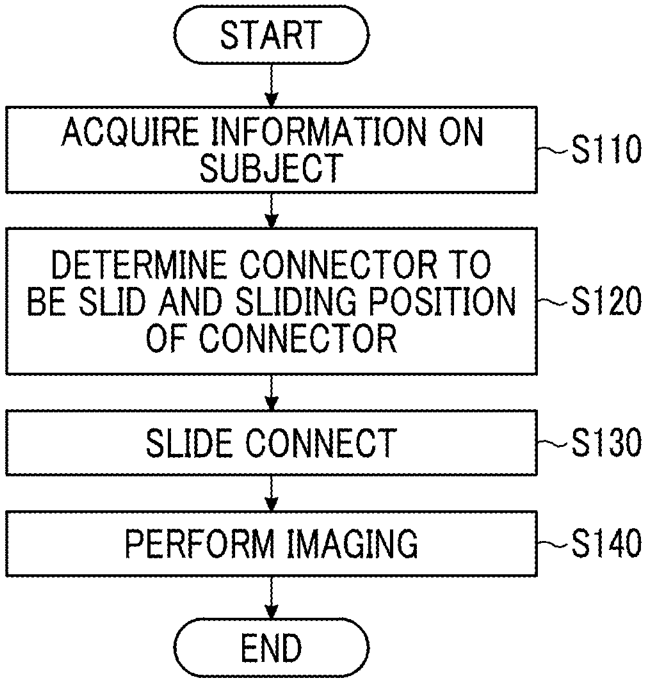
FIG. 19 is a flowchart of sliding control of the connector.

FIG. 19 is a flowchart showing processing of the sliding control of the connector. For example, in a case in which the user operates the operation panel 317 to issue an instruction to start the sliding of the connector 322, the subject information acquisition unit (processor 352) acquires the information on the subject (step S110). The information on the subject may include an imaging condition in addition to the information on the subject, such as a name, ID, an age, a height, or a weight. The imaging condition may include an imaging part (which position of the top plate is installed at the magnetic field center (imaging center)) and a body orientation of the subject (whether the subject enters the magnetic field from the head or from the foot, whether the subject is in a prone state or in a supine state). The imaging condition may include information on the coil (which coil is used, the number of cables of the coil, the cable length, or the like). The user may input the information on the subject from the input device 210 (see FIG. 2), or may issue an instruction to use the information already stored in the external storage device 180 or the like. The user may input necessary information from the operation panel 317 of the examination table apparatus 300.

The sliding controller 352E (processor 352) determines a sliding target connector (connector to be slid) among the plurality of connectors and a sliding position of the sliding target connector based on the acquired information (step S120), and slides the sliding target connector to the sliding position (step S130). The processor 352 may notify of a case in which the sliding is completed or a case in which the sliding cannot be executed due to some problem, by turning on a lamp or a switch, displaying an image, a character, or the like, or performing audio output. This notification may be issued on the operation panel 317.

After the sliding of the connector 322 is completed, the cable of the coil is connected to the connector 322. The user may perform the connection by himself/herself, or a connection mechanism (not shown) may be provided to automatically perform the connection. It is preferable that the connection detection unit 352C (processor 352) detects the connection and issues notification in the same manner as in a case of the completion of the sliding. In a case in which the connection is completed, the imaging of the subject is performed in accordance with a predetermined sequence under the control of the controller 170 of the magnetic resonance imaging apparatus 100 or the like (step S140).

After the imaging is terminated, the cable is removed by the user or automatic control, but it is preferable that the connection detection unit 352C (processor 352) detects the removal in the same manner as in a case of the connection, and issues the notification. In a case in which the removal of the cable (coil) is detected, it is preferable that the sliding controller 352E (processor 352) automatically slides (returns) the connector 322 to a predetermined position after a lapse of a predetermined time (not particularly limited, but for example, about several seconds). In addition, in a case in which another examination information (imaging schedule) is set, the processor 352 may acquire the examination information and slide the connector 322.

Although the embodiments according to the present invention has been described above, it goes without saying that the present invention is not limited to the above-described embodiments, and various modifications can be made.

EXPLANATION OF REFERENCES

10: magnetic resonance imaging system
100: magnetic resonance imaging apparatus
101: apparatus body
102: tunnel
300: examination table apparatus
310: top plate
311: top plate holding part
313: top plate raising/lowering mechanism
315: top plate lock mechanism
317: operation panel
320: opening
322: connector
340: body part

What is claimed is:

1. An examination table apparatus used in a medical imaging apparatus, the examination table apparatus comprising:

a top plate on which a subject is placed;

a plurality of connectors that are provided on the top plate and that connect a coil for capturing an image of the subject; and a plurality of support members that support the plurality of connectors, wherein the plurality of connectors are provided on both sides of the top plate in a lateral direction, with one or more connectors on each side, and are slidable with respect to the top plate in a part of the top plate in a longitudinal direction, wherein a plurality of openings or a plurality of grooves are formed on both sides of the top plate in the lateral direction, in a part of the top plate in the longitudinal direction, wherein the plurality of connectors are slidable in the plurality of openings or the plurality of grooves, wherein a plurality of holding members that hold the plurality of support members are disposed on both sides of the top plate in the lateral direction and projected in the longitudinal direction and are fixed to the top plate, and wherein the plurality of support members are slid with respect to the plurality of holding members to slide the plurality of connectors with respect to the top plate.

2. The examination table apparatus according to claim 1, wherein the holding member holds a horizontal-direction end part of the support member.

3. The examination table apparatus according to claim 1, wherein the holding member holds at least a part of a vertical-direction lower surface of the support member.

4. The examination table apparatus according to claim 1, wherein a gap between the plurality of connectors and the plurality of openings or the plurality of grooves is shielded by at least one of the support member or the holding member.

5. The examination table apparatus according to claim 1, further comprising:

a processor; and a sliding mechanism that moves the plurality of connectors in the longitudinal direction, wherein the processor is configured to:

acquire information on the subject; and slide the plurality of connectors by controlling the sliding mechanism based on the acquired information.

6. The examination table apparatus according to claim 5, wherein the processor is configured to:

acquire an imaging condition of a medical image for the subject as the information on the subject.

7. The examination table apparatus according to claim 5, wherein the processor is configured to:

determine a sliding target connector among the plurality of connectors and a sliding position of the sliding target connector, based on the acquired information, and slide the sliding target connector to the sliding position.

8. The examination table apparatus according to claim 1, wherein, in a case in which the subject in a state in which the coil is attached to the subject is placed on the top plate, the plurality of connectors are movable to a position overlapping a range in which the coil is present in the longitudinal direction of the top plate.

9. The examination table apparatus according to claim 1, wherein the plurality of connectors are slidable independently of each other.

10. The examination table apparatus according to claim 1, wherein one connector among the plurality of connectors and the other connector among the plurality of connectors are slidable in conjunction with each other.

11. The examination table apparatus according to claim 1, wherein the medical imaging apparatus is a magnetic resonance imaging apparatus.

12. A medical imaging system comprising:
the examination table apparatus according to claim 1; and
the medical imaging apparatus.

13. The medical imaging system according to claim 12, wherein at least one of coils for imaging different parts of the subject is connected to one connector and at least another one of the coils is connected to the other connector among the plurality of connectors.

14. The medical imaging system according to claim 12, wherein a coil for imaging a specific part of the subject is connectable to
one connector provided on one side of the top plate in the lateral direction of the top plate among the plurality of connectors, and
the other connector provided on the other side of the top plate in the lateral direction of the top plate among the plurality of connectors.

* * * * *